(12) United States Patent
Tachaboonyakiat et al.

(10) Patent No.: US 7,829,337 B2
(45) Date of Patent: Nov. 9, 2010

(54) CELL-RELEASING AGENT AND METHOD OF RELEASING CELL SHEET

(75) Inventors: Wanpen Tachaboonyakiat, Bangkok (TH); Masakazu Kato, Aichi (JP); Tooru Ooya, Ishikawa (JP); Nobuhiko Yui, Ishikawa (JP)

(73) Assignees: Japan Science And Technology Agency, Kawaguchi-shi (JP); Japan Tissue Engineering Co., Ltd., Gamagori-shi (JP); Japan Advanced Institute of Science And Technology, Nomi-shi (JP)

( * ) Notice: Subject to any disclaimer, the term of this patent is extended or adjusted under 35 U.S.C. 154(b) by 710 days.

(21) Appl. No.: 11/663,744

(22) PCT Filed: Sep. 9, 2005

(86) PCT No.: PCT/JP2005/016633

§ 371 (c)(1),
(2), (4) Date: Mar. 30, 2007

(87) PCT Pub. No.: WO2006/038427

PCT Pub. Date: Apr. 13, 2006

(65) Prior Publication Data

US 2008/0038821 A1 Feb. 14, 2008

(30) Foreign Application Priority Data

Sep. 30, 2004 (JP) ............................. 2004-286163

(51) Int. Cl.
| | | |
|---|---|---|
| *C12N 5/00* | (2006.01) | |
| *C12N 5/02* | (2006.01) | |
| *C07C 229/00* | (2006.01) | |
| *C08B 30/18* | (2006.01) | |

(52) U.S. Cl. .......................... 435/378; 560/169; 536/46
(58) Field of Classification Search ................. 435/378; 560/169; 536/46

See application file for complete search history.

(56) References Cited

U.S. PATENT DOCUMENTS

2004/0185085 A1    9/2004   Ochi et al.

FOREIGN PATENT DOCUMENTS

| JP | A 6-104061 | 4/1994 |
| JP | A 2004-135571 | 5/2004 |
| WO | WO 03/011353 A1 | 2/2003 |
| WO | WO 03011353 A1 * | 2/2003 |
| WO | WO 03/074099 A1 | 9/2003 |
| WO | WO 2004/027040 A2 | 4/2004 |

OTHER PUBLICATIONS

Ooya et al.; "Synthesis of theophyline-polyrotaxane conjugates and their drug release via supramolecular dissociation;" *Journal of Controlled Release*; vol. 58; 1999; pp. 251-269; Elsevier Science B.V.

Tomoyuki Furubayashi et al., "Hydrolyzability for optimization of cartilage tissue regeneration environment, Control of properties of polyrotaxane hydrogel," The Society of Polymer Science, Japan, Summary of the Symposium on Macromolecules, 2003, vol. 32, pp. 45-46.

* cited by examiner

*Primary Examiner*—Shaojia Anna Jiang
*Assistant Examiner*—Everett White
(74) *Attorney, Agent, or Firm*—Oliff & Berridge, PLC

(57) ABSTRACT

A cell-sheet releasing agent of the present invention contains an aminated polyrotaxane. The polyrotaxane constituting the skeleton of the cell-releasing agent of the present invention has a structure in which cavities of a plurality of cyclic molecules are threaded onto a linear molecule and both terminals of the linear molecule have a bulky cap bonded thereto so that the cyclic molecules are not dethreaded from the linear molecule. Furthermore, the aminated polyrotaxane contained in the cell-releasing agent of the present invention is a compound in which at least some of hydroxy groups in the cyclodextrin structure contained in the polyrotaxane are each substituted with a substituent having an amino group. According to this cell-sheet releasing agent, cultured cells anchored to the surface of a container can be released without damaging the cells and without controlling the temperature.

9 Claims, 1 Drawing Sheet

CELL-RELEASING AGENT AND METHOD OF RELEASING CELL SHEET

TECHNICAL FIELD

The present invention relates to a cell-releasing agent and a method of releasing a cell sheet.

BACKGROUND ART

A cell sheet cultured in a container is anchored to the surface of the container, and the cell sheet may be released from the surface of the container using a protease such as Dispase (registered trademark) in order to recover this cell sheet. In such a releasing procedure using a protease, not only may the cells be damaged, but also the extracellular matrix produced during the culture may also be decomposed. Furthermore, since most proteases are materials derived from animals, the application of such proteases to a cell sheet for regenerative medicine is problematic in terms of safety. In view of this point, for example, JP-A 6-104061 proposes a method of releasing cultured cells anchored to the surface of a container without using a protease to recover the cells. More specifically, a Petri dish whose surface is covered with poly (N-isopropylacrylamide) is prepared, and bovine aortic endothelial cells are cultured at 37° C. on the Petri dish. The Petri dish is then cooled to 4° C. to change the surface of the Petri dish from hydrophobic to hydrophilic, thereby releasing and recovering the cultured cells.

DISCLOSURE OF INVENTION

However, according to the above-cited patent publication, since the temperature must be controlled to release the cultured cells, the procedure is not simple.

It is an object of the present invention to provide a cell-releasing agent with which cells anchored to the surface of a container can be released by a simple procedure. It is another object of the present invention to provide a method of releasing a cell sheet anchored to the surface of a container using the cell-releasing agent.

In order to achieve at least a part of the above objects, the present invention is constructed as follows.

A cell-sheet releasing agent of the present invention contains an aminated polyrotaxane. According to this cell-sheet releasing agent, cultured cells anchored to the surface of a container can be released without damaging the cells and without controlling the temperature.

The polyrotaxane constituting the skeleton of the cell-releasing agent of the present invention has a structure in which cavities of a plurality of cyclic molecules are threaded onto a linear molecule and both terminals of the linear molecule have a bulky cap bonded thereto so that the cyclic molecules are not dethreaded from the linear molecule.

The linear molecule is preferably at least one compound selected from the group consisting of polyethylene glycol, polypropylene glycol, star-shaped polyethylene glycol, a copolymer of polyethylene glycol and polypropylene glycol, polyvinyl ether, highly-branched polyether, highly-branched oligoethylene glycol, highly-branched oligopropylene glycol, poly(trimethylene oxide), poly(ε-caprolactone), polylactic acid, a copolymer of poly(ε-caprolactone) and polylactic acid, a copolymer of polylactic acid and polyethylene glycol, poly(ε-lysine), polyamide, poly(iminooligomethylene), ionene, poly(vinyldiene chloride), polypropylene, oligopropylene, polyethylene, oligoethylene, poly(alkylenebenzimidazole), polyurethane, poly(viologen), poly(N-dimethyldecamethylene ammonium), poly(dimethylsiloxane), polyaniline, polycarbonate, poly(methyl methacrylate), poly(N-acylethyleneimine), polyethyleneimine, a composite of poly(4-vinylpyridine) and dodecylbenzenesulfonic acid, a polyethylene glycol-modified fullerene, hydrophobic polysaccharide, a graft copolymer of polyethylene glycol and polysaccharide, a graft copolymer of polypropylene glycol and polysaccharide, and diphenylhexatriene. The average molecular weight of this linear molecule is preferably in the range of 200 to 1,000,000, more preferably in the range of 400 to 50,000, and particularly preferably in the range of 1,000 to 5,000.

The cyclic molecule is preferably α-, β-, or γ-cyclodextrin, but may be a compound having a cyclic structure similar to these. Examples of the compound having such a cyclic structure include cyclic polyethers, cyclic polyesters, cyclic polyetheramines, and cyclic polyamines. A preferred combination of the linear molecule and the cyclic molecule is the combination of α-cyclodextrin and polyethylene glycol.

The bulky cap is not particularly limited as long as it has a structure that prevents the cyclic molecules from being dethreaded, but is preferably a biocompatible group having a bulky substituent. The bulky cap is preferably introduced into each terminal of the linear molecule with a hydrolyzable bond therebetween. The biocompatible group is not particularly limited as long as the biocompatible group is a group having a high compatibility with the living body (a group having a high degree of safety for the living body). For example, the biocompatible group is preferably an amino acid, an oligopeptide, an oligosaccharide, or a saccharide derivative. Examples of the amino acid include alanine, valine, leucine, isoleucine, methionine, proline, phenylalanine, tryptophan, aspartic acid, glutamic acid, glycine, serine, threonine, tyrosine, cysteine, lysine, arginine, and histidine. Examples of the oligopeptide include oligopeptides in which a plurality of the above amino acids are combined with peptide bonds. Examples of the oligosaccharide include oligosaccharides whose number of repeating units is in the range of about 1 to 10 and which are composed of a monosaccharide constituting a polysaccharide such as dextran, hyaluronic acid, chitin, chitosan, alginic acid, chondroitin sulfate, or starch; and cyclic oligosaccharides such as α-, β-, and γ-cyclodextrin. Examples of the saccharide derivative include compounds prepared by performing a chemical modification, such as acetylation or isopropylation, of an oligosaccharide, a polysaccharide, or a monosaccharide. Among these, an amino acid having a benzene ring, such as L-phenylalanine, L-tyrosine, or L-tryptophan, is preferred. The bulky substituent is not particularly limited as long as the substituent can prevent the cyclic molecules from being dethreaded from the linear molecule. For example, a group having at least one benzene ring or a group having at least one tertiary butyl group is preferred. Examples of the group having at least one benzene ring include a benzyloxycarbonyl (Z) group, a 9-fluorenylmethyloxycarbonyl (Fmoc) group, and a benzylester (OBz) group. Examples of the group having at least one tertiary butyl group include a tertiary butylcarbonyl (Boc) group and an amino acid tert-butylester (OBu) group. Among these, a benzyloxycarbonyl group is preferred. The hydrolyzable bond is preferably a bond that is hydrolyzed in the living body. From the standpoint that the bond is immediately non-enzymatically hydrolyzed in the living body, the hydrolyzable bond is preferably an ester bond.

The aminated polyrotaxane contained in the cell-releasing agent of the present invention may be a compound in which at least some of hydroxy groups in the cyclodextrin structure contained in the polyrotaxane are each substituted with a substituent having an amino group. In this case, the hydroxy group in the cyclodextrin structure is preferably a hydroxy group of glucose constituting the cyclodextrin structure, and more preferably a hydroxy group at the 6th position of the glucose. The substituent having an amino group is not particularly limited but is preferably represented by —OOCNH-A-NR$^1$R$^2$ (where A represents a linear or branched hydrocarbon chain, and R$^1$ and R$^2$ may be the same or different and each represent a hydrogen atom or a linear or branched hydrocarbon group). In the formula, A is preferably a linear or branched hydrocarbon chain having 2 to 4 carbon atoms. Examples of the hydrocarbon chain include —(CH$_2$)$_2$—, —CH(CH$_3$)CH$_2$—, —CH$_2$CH(CH$_3$)—, —(CH$_2$)$_3$—, —CH(CH$_2$CH$_3$)CH$_2$—, —CH$_2$CH(CH$_2$CH$_3$)—, —CH(CH$_3$)CH$_2$CH$_2$—, —CH$_2$CH(CH$_3$)CH$_2$—, —CH$_2$CH$_2$CH(CH$_3$)—, and —(CH$_2$)$_4$—. Each of R$^1$ and R$^2$ is preferably a hydrogen atom or a linear or branched hydrocarbon group having 1 to 5 carbon atoms. Examples of the latter hydrocarbon group include a methyl group, an ethyl group, a n-propyl group, an isopropyl group, a n-butyl group, an isobutyl group, a sec-butyl group, and a tert-butyl group. It is believed that the site of —OOCNH— functions as a joining portion, and thus the structure of the site is not limited thereto. Alternatively, the site may be, for example, —OCOO—, —OOC—, —OCH$_2$—, —OC(OH)CH$_2$—, or —OC(=S)NH—.

The cell-releasing agent of the present invention is used for releasing cells (anchorage-dependent cells) anchored to the surface of a container. Examples of the anchorage-dependent cells include chondrocytes, osteoblasts, fibroblasts, epidermal cells, epithelial cells, adipocytes, hepatocytes, pancreatic cells, muscle cells, and precursor cells thereof, mesenchymal stem cells, and embryonic stem cells (ES cells).

The cell-releasing agent of the present invention is suitable for use in releasing a cell sheet, in particular, a cell sheet of epidermal cells, anchored to the surface of a container. A method of releasing the cell sheet may include a culture step of anchoring cells to the surface of a container and culturing the cells to form a cell sheet, and a subsequent releasing step of releasing the cell sheet from the surface of the container using a culture medium containing the cell-sheet releasing agent of the present invention. Herein, the culture medium may be any liquid in which most of the cells constituting the cell sheet remain viable during the releasing step. Examples of the culture medium include not only a basal media such as a DMEM, and media for growth prepared by adding a growth factor to a basal medium, but also liquids such as physiological saline and a phosphate buffer. The method of releasing the cell sheet may further include a subsequent recovery step of recovering the released cell sheet. In the releasing step, the cell sheet may be gradually released from the surface of the container while the cells are cultured. In the recovery step, the released cell sheet may be contacted by a supporting film for suspension and then recovered by pulling up the supporting film. The supporting film for suspension is not particularly limited as long as the cells grown to a predetermined state can be suspended in a substantially intact state. Examples of the supporting film include sterile gauze; sterile Japanese paper; sterile filter paper; sterile non-woven fabrics; hydrophilic films such as a polyvinylidene fluoride (PVDF) film and a polytetrafluoroethylene (PTFE) film; and sheets made of a flexible polymer material such as a silicone rubber, a biodegradable polymer such as polyglycolic acid or polylactic acid, or hydrogel such as an agar medium, collagen gel, or gelatin gel.

EXAMPLES

Example 1

Figure 1:
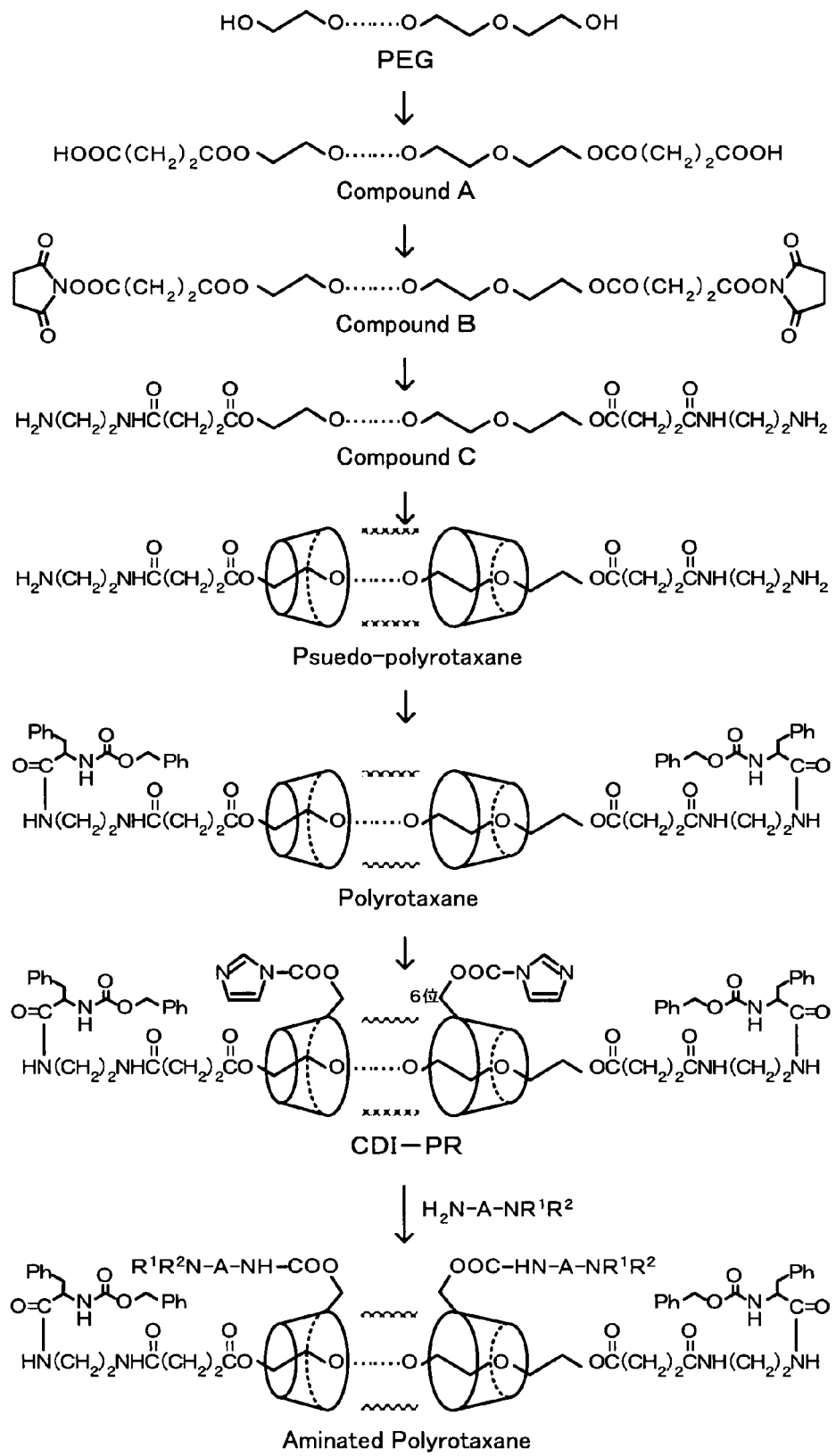
FIG. 1 is a drawing illustrating a synthesis procedure of an aminated polyrotaxane.

A polyrotaxane (see FIG. 1) was synthesized by a procedure described below.

[1-1] Synthesis of PEG Having an Amino Group at Each Terminal with an Ester Bond Therebetween Polyethylene glycol (PEG) (33 g, 10 mmol) having a molecular weight of 3,300 and succinic anhydride (20 g, 200 mmol) were dissolved in toluene (220 mL), and the resulting solution was refluxed at 150° C. for five hours. After the completion of the reaction, the reaction solution was poured into an excessive amount of diethyl ether. The precipitate was then separated by filtration and dried under reduced pressure to prepare a crude product. The crude product was dissolved in dichloromethane, and insoluble matter was then removed by centrifugal separation. The solution was poured into an excessive amount of diethyl ether. The precipitate was then separated by filtration and dried under reduced pressure. As a result, PEG having a carboxyl group at each terminal (Compound A) was obtained in the form of a white powder. Compound A (20 g, 5.7 mmol) and N-hydroxysuccinimide (HOSu) (17.1 g, 148.2 mmol) was dissolved in a mixed solution (350 mL, volume ratio: 1:1) of 1,4-dioxane and dichloromethane. The solution was cooled with ice, and dicyclohexylcarbodiimide (DCC) (23.5 g, 114 mmol) was then added thereto. The mixture was stirred for one hour while being cooled with ice and then stirred at room temperature overnight. Dicyclohexylurea, which was a byproduct, was separated by filtration. The filtrate was concentrated and then poured into an excessive amount of diethyl ether. The precipitate was then separated by filtration and dried under reduced pressure. As a result, PEG having activated carboxyl groups (Compound B) was obtained in the form of a white powder. Subsequently, dichloromethane (75 mL) containing Compound B (10 g, 2.7 mmol) was added dropwise to dichloromethane (75 mL) containing ethylenediamine (0.4 mL, 6 mmol). After the completion of dropwise addition, the solution was stirred for one hour at room temperature. After the completion of the reaction, the solution was poured into an excessive amount of diethyl ether. The precipitate was then separated by filtration and dried under reduced pressure. As a result, PEG having an amino group at each terminal (Compound C) was obtained in the form of a white powder.

[1-2] Preparation of a Pseudo-Polyrotaxane

An aqueous solution (20 mL) of Compound C (4 g, 1.12 mmol) was added dropwise to a saturated aqueous solution (311 mL) of α-cyclodextrin (α-CD) (48 g, 49.2 mmol) at room temperature. The solution was stirred for one hour while ultrasonic waves were applied thereto and then stirred at room temperature for 24 hours. A white precipitate was recovered by centrifugal separation and then dried under reduced pressure at 50° C. to obtain a pseudo-polyrotaxane in the form of a white powder. The term "polyrotaxane" means a compound in which cavities of a plurality of cyclic molecules (e.g., cyclodextrin) are threaded onto a linear molecule (e.g., PEG) and each terminal of the linear molecule is capped with a bulky substituent. The term "pseudo-polyrotaxane" means a compound in which each terminal of the polyrotaxane has not yet been capped with a bulky substituent.

[1-3] Preparation of a Terminal Capping Agent

In order to introduce benzyloxycarbonyl-L-phenylalanine (Z-L-Phe, wherein Z represents a benzyloxycarbonyl group) as a bulky substituent for preventing α-CD from being dethreaded, activation of the carboxyl group of Z-L-Phe was performed. More specifically, Z-L-Phe (100 g, 334 mmol) was dissolved in 1,4-dioxane (800 mL), and HOSu (38.42 g, 334 mmol) was added to the solution while the solution was cooled with ice. One hour later, a 1,4-dioxane solution (200 mL) containing DCC (75.7 g, 367 mmol) was gradually added to the solution. The mixture was stirred for one hour while being cooled with ice and then stirred at room temperature overnight. Dicyclohexylurea, which was a byproduct, was separated by filtration. The filtrate was concentrated and then poured into an excessive amount of diethyl ether. The precipitate was then separated by filtration and dried under reduced pressure to prepare a crude product. The crude product was dissolved in dichloromethane at room temperature so that the concentration was as close to the saturated concentration as possible. An appropriate amount of petroleum ether was then added to the solution and the solution was kept in cold storage to perform recrystallization. The crystals were separated by filtration and dried under reduced pressure. As a result, succinimide ester of Z-L-Phe (Z-L-Phe-OSu) was obtained in the form of white needle crystals.

[1-4] Preparation of a Polyrotaxane

Z-L-Phe-OSu (80 g, 200 mmol) was dissolved in dimethyl sulfoxide (DMSO) (60 mL), and the pseudo-polyrotaxane (45 g, 2 mmol) was added to the solution. DMSO was added to the resulting heterogeneous solution gradually under stirring at room temperature for 96 hours so that the solution became homogeneous. After the completion of the reaction, the reaction solution was poured into an excessive amount of diethyl ether to prepare a crude product. The crude product was washed with acetone and dimethylformamide (DMF) in that order to remove impurities (such as unreacted Z-L-Phe-OSu, α-CD, and Compound C). The product was then separated by filtration and dried under reduced pressure to obtain a biodegradable polyrotaxane in the form of a white powder. The synthesis of the product was confirmed by $^1$H-NMR. The number of threaded α-CD molecules of this polyrotaxane was also determined by $^1$H-NMR from the integral ratio of the protons in PEG and the protons at the first position of carbon (C) of α-CD molecules. According to the result, the number of α-CD molecules was 17.

Example 2

A CDI-activated polyrotaxane was prepared by a procedure described below. The polyrotaxane (1 g, 0.0369 mol, CD=0.871 mmol, OH=15.6 mmol) obtained in Example 1 was dissolved in DMSO (10 mL) in a nitrogen atmosphere, and 2.54 g of N,N'-carbonyldiimidazole (CDI) (15.6 mmol, which was equivalent to the hydroxy group in the polyrotaxane) was then added to the solution. The reaction was conducted in a nitrogen atmosphere at room temperature. Three hours later, the solution was added dropwise to ether to produce a white precipitate. The precipitate was separated by filtration and dried under reduced pressure at room temperature to obtain the CDI-activated polyrotaxane (CDI-PR) in the form of a white powder. The activation ratio of this CDI-PR was calculated from an absorbance at 207 nm with an ultraviolet absorption spectrometer. According to the result, the activation ratio was 91.37%.

Example 3

Aminated polyrotaxanes, a sulfonated polyrotaxane, and a carboxylated polyrotaxane were prepared as described below.

Aminated polyrotaxanes were prepared by a procedure described below. Namely, 1 g of the CDI-PR (0.029 mmol) prepared in Example 2 was dissolved in 20 mL of dimethyl sulfoxide (DMSO). An excessive amount of an amination reagent was added to the solution, and the solution was stirred at room temperature for three hours. Subsequently, the reaction solution was poured into an excessive amount of diethyl ether. The resulting precipitate was washed with the same solvent to prepare a target aminated polyrotaxane. In this experiment, an aminated polyrotaxane prepared using 1,2-diaminopropane as the amination reagent was referred to as Sample No. 1 (the number of introduced amine molecules: 16, the number of threaded α-CD molecules: 17), an aminated polyrotaxane prepared using 1,3-diaminopropane was referred to as Sample No. 2 (the number of introduced amine molecules: 38, the number of threaded α-CD molecules: 17), an aminated polyrotaxane prepared using N,N-dimethyl-1,2-diaminoethane was referred to as Sample No. 3 (the number of introduced amine molecules: 158, the number of threaded α-CD molecules: 17), and an aminated polyrotaxane prepared using N,N-dimethyl-1,3-diaminopropane was referred to as Sample No. 4 (the number of introduced amine molecules: 128, the number of threaded α-CD molecules: 17).

A carboxylated polyrotaxane was prepared by a procedure described below. In accordance with Example 1, a polyrotaxane in which each terminal of PEG (molecular weight: 4,000) threading cavities of a large number of α-CD molecules was capped with Z-tyrosine was prepared. By esterification of this polyrotaxane by succinic anhydride, the water-soluble carboxylated polyrotaxane in which carboxyethylester (CEE) groups were introduced in hydroxy groups of α-CD molecules (the number of introduced CEE groups: 188, the number of threaded α-CD molecules: 15). This carboxylated polyrotaxane was referred to as Sample No. 5.

A sulfonated polyrotaxane was prepared by a procedure described below. Taurine was introduced into the carboxylated polyrotaxane synthesized as described above using water-soluble carbodiimide as a condensing agent to prepare a sulfonated polyrotaxane (the number of introduced taurine molecules: 117, the number of threaded α-CD molecules: 9). This sulfonated polyrotaxane was referred to as Sample No. 6. The polyrotaxane obtained in Example 1 was referred to as Sample No. 7. Structural characteristics of these samples are shown in Table 1.

TABLE 1

| | PEG | | | Substituent | | |
|---|---|---|---|---|---|---|
| Sample No. | Molecular weight | Number of pierced α-CD molecules | Reagent | | Number of introduced molecules to polyrotaxane | Structure (—OOCNH-A-NR$^1$R$^2$) |
| 1 | 3,300 | 17 | Primary amine (1,2-diaminopropane) | | 16 | —OOCNH—CH(CH$_3$)CH$_2$—NH$_2$ or —OOCNH—CH$_2$CH(CH$_3$)—NH$_2$ |

TABLE 1-continued

| | PEG | | | Substituent | |
|---|---|---|---|---|---|
| Sample No. | Molecular weight | Number of pierced α-CD molecules | Reagent | Number of introduced molecules to polyrotaxane | Structure (—OOCNH-A-NR$^1$R$^2$) |
| 2 | 3,300 | 17 | Primary amine (1,3-diaminopropane) | 38 | —OOCNH—(CH$_2$)$_3$—NH$_2$ |
| 3 | 3,300 | 17 | Tertiary amine (N,N-dimethyl-1,2-diaminoethane) | 158 | —OOCNH—(CH$_2$)$_2$—N(CH$_3$)$_2$ |
| 4 | 3,300 | 17 | Tertiary amine (N,N-dimethyl-1,3-diaminopropane) | 128 | —OOCNH—(CH$_2$)$_3$—N(CH$_3$)$_2$ |
| 5 | 4,000 | 28 | Succinic anhydride | 188 | —O(CH$_2$)$_2$COOH |
| 6 | 4,000 | 9 | Taurine | 117 | —O(CH$_2$)$_2$CONH—(CH$_2$)$_2$—SO$_3$H |
| 7 | 3,300 | 17 | — | — | —OH |

Example 4

A cell-releasing test was performed using the polyrotaxane of each sample by a procedure described below. The polyrotaxane of each sample was accurately weighed, and 70% ethanol was then added to the polyrotaxane to prepare a solution or a suspension having a concentration of 200 m/mL. Subsequently, a dilution series having concentrations in the range of 0.02 to 20 mg/mL was prepared with 70% ethanol. These samples were charged on a 96-hole plate in an amount of 100 μL and dried in a clean bench for one night under air flow. Subsequently, 100 μL of a culture medium for cell growth was added to each sample and the mixture was stirred for one hour to again dissolve the polyrotaxane. Subsequently, 100 μL of an NIH3T3 cell suspension (high density condition: 3×10$^5$ cells/mL, medium density condition: 9×10$^4$ cells/mL, low density condition: 3×10$^4$ cells/mL) was added to each sample. The final polyrotaxane concentrations were 0.01, 0.1, 1, and 10 mg/mL, and the NIH3T3 cell densities were 1×10$^4$, 3×10$^4$, and 10×10$^4$ cells/cm$^2$. The samples were then cultured under a condition of 5% CO$_2$ at 37° C. until the eighth day from the start of culturing and observed with a microscope.

As a result, in the culture media containing the carboxylated polyrotaxane (Sample No. 5), the sulfonated polyrotaxane (Sample No. 6), and the polyrotaxane in which the hydroxy groups of α-CD molecules were not substituted (Sample No.7), regardless of the seeding density, when the concentration was 1 mg/mL or less, the cells were merely anchored on the plate surface and grown, and were not released. In the above culture media, when the concentration was 10 mg/mL, the cells were neither anchored nor grown.

In contrast, in the aminated polyrotaxanes in which a primary amine was introduced (Sample Nos. 1 and 2), when the concentration was in the range of 0.1 to 1 mg/mL and the seeding density was the medium and high density conditions, until the third day from the start of culturing, the cells were grown in the form of a sheet and released, and the cells were further contracted to form a single spheroid. This result suggested that the aminated polyrotaxanes were weakly bonded to the cells to partly inhibit the anchoring of the cells on the plate surface, and after the formation of the sheet, the contractive force of the cell sheet exceeded the adhesive force between the plate surface and the cells and the cells were released in the form of a sheet. Therefore, the cell sheet can be recovered using a cell sheet support at the stage of the sheet before the spheroid is formed. In the above aminated polytaxanes, when the concentration was 10 mg/mL and the seeding density was the medium and high density conditions, cell colonies were aggregated to form a large number of small spheroids on the first day from the start of culturing. This result suggested that the amount of bonding between the aminated polyrotaxanes and the cells was larger than that in the case where the cells were released in the form of a sheet to form a single spheroid, and the sheet contractive force of the cell colonies exceeded the adhesive force between the plate surface and the cells at the stage of the formation of small colonies.

On the other hand, in the aminated polyrotaxanes in which a tertiary amine was introduced (Sample Nos. 3 and 4), when the concentration was 10 mg/mL and the seeding density was the high density condition, cell colonies were aggregated to form a large number of small spheroids until the second day or the third day from the start of culturing. In the above aminated polyrotaxanes, when the concentration was the same as the above and the seeding density was the medium and low density conditions, the cells were merely anchored on the plate surface and grown. This result suggested that, in these aminated polyrotaxanes in which a tertiary amine was introduced, the anchoring property for the cells was lower than that of the aminated polyrotaxanes in which a primary amine was introduced.

In the above-described cell-releasing test, a culture step and a releasing step were performed at the same time. Alternatively, an aminated polyrotaxane may be added immediately before the cells become confluent in the culture step. In such a case, the cells are released from the surface of the container by a sheet contractive force while cells are grown to form a sheet. Accordingly, for example, a hydrophilic-treated polyvinylidene fluoride (PVDF) film may be dropped from the upper part so that the cell sheet is brought into contact with the PVDF film, and the cell sheet may then be taken up together with the film. Thus, the cell sheet can be released and recovered.

This application claims the priority of Japanese Patent Application No. 2004-286163 filed Sep. 30, 2004, the entire contents of which are incorporated herein by reference.

INDUSTRIAL APPLICABILITY

The present invention can be used in the field of regenerative medicine.

The invention claimed is:
1. A method of releasing a cell sheet comprising:
   a culture step of anchoring cells to the surface of a container and culturing the cells to form a cell sheet; and
   a releasing step of releasing the cell sheet from the surface of the container using a culture medium in which a cell-releasing agent comprising an aminated polyrotaxane is dissolved, after the culture step, wherein the aminated polyrotaxane is a compound in which at least some of hydroxy groups in the cyclodextrin structure contained in the polyrotaxane are each substituted with a substituent having an amino group.

2. The method according to claim 1, wherein the polyrotaxane is a compound in which cavities of a plurality of the cyclodextrin are threaded onto a linear molecule and both terminals of the linear molecule are each introduced with a biocompatible group having a bulky substituent with a hydrolyzable bond therebetween.

3. The method according to claim 2, wherein the substituent having an amino group is represented by —OOCNH-A-N$R^1R^2$ wherein A represents a linear or branched hydrocarbon chain, and $R^1$ and $R^2$ are the same or different and each represent a hydrogen atom or a linear or branched hydrocarbon group.

4. The method according to claim 3, wherein A is a linear or branched hydrocarbon chain having 2 to 4 carbon atoms.

5. The method according to claim 3, wherein $R^1$ and $R^2$ are the same or different and each represent a hydrogen atom or a linear or branched hydrocarbon group having 1 to 5 carbon atoms.

6. The method according to claim 1, wherein the substituent having an amino group is represented by —OOCNH-A-N$R^1R^2$ wherein A represents a linear or branched hydrocarbon chain, and $R^1$ and $R^2$ are the same or different and each represent a hydrogen atom or a linear or branched hydrocarbon group.

7. The method according to claim 6, wherein A is a linear or branched hydrocarbon chain having 2 to 4 carbon atoms.

8. The method according to claim 6, wherein $R^1$ and $R^2$ are the same or different and each represent a hydrogen atom or a linear or branched hydrocarbon group having 1 to 5 carbon atoms.

9. The method of releasing a cell sheet according to claim 1, further comprising:
a recovery step of recovering the released cell sheet.

* * * * *